Nov. 29, 1966 W. E. LAMMERTS Plant Pat. 2,687
ROSE PLANT
Filed Aug. 31, 1965
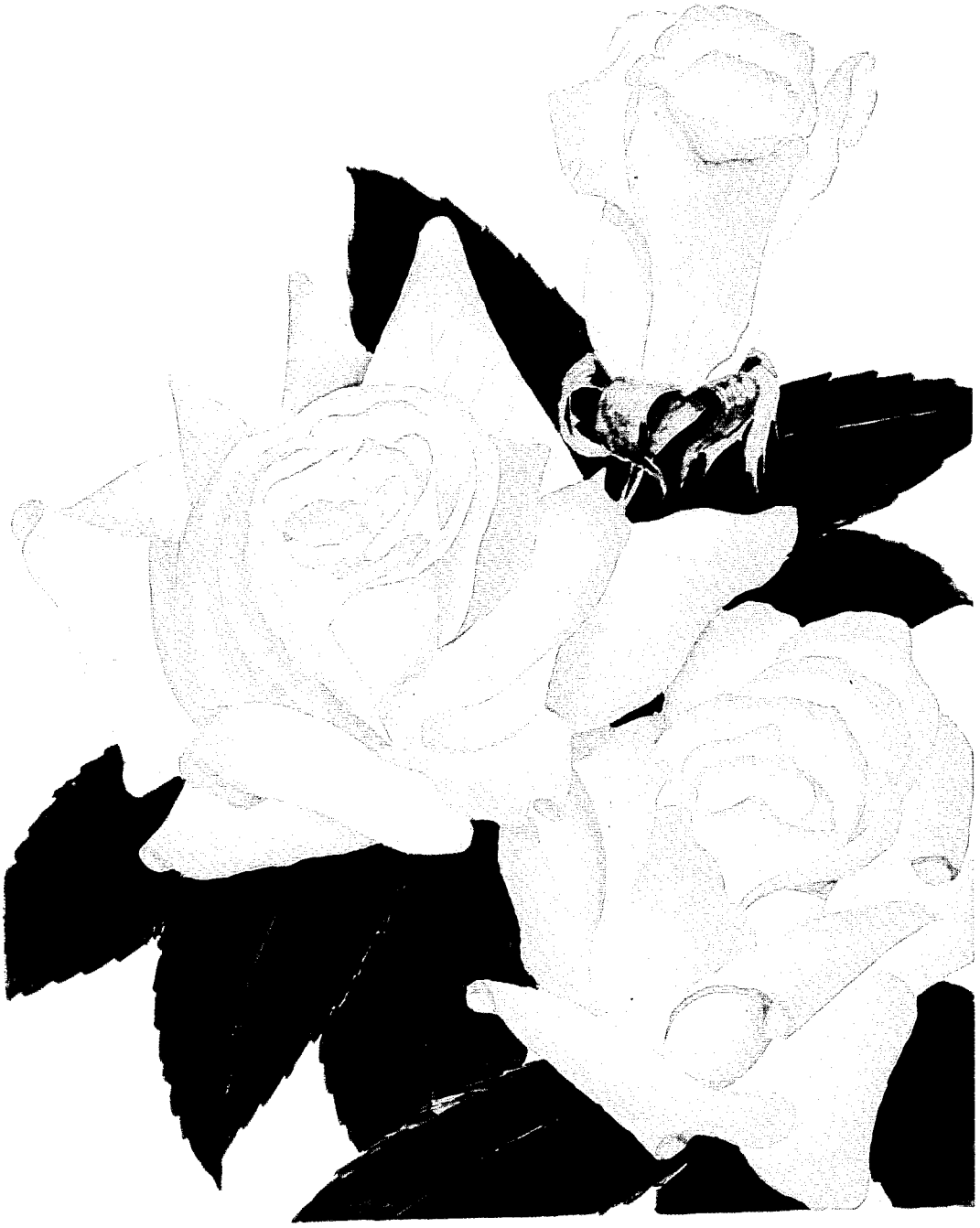
WITNESS
Samuel H. Groff
INVENTOR
WALTER E. LAMMERTS
by Rummler & Snow
ATTYS.

United States Patent Office

Plant Pat. 2,687

Patented Nov. 29, 1966

2,687

ROSE PLANT

Walter E. Lammerts, Watsonville, Calif., assignor to Amling-Devor Nurseries, Inc., Livermore, Calif., a corporation of California Filed Aug. 31, 1965, Ser. No. 484,141
1 Claim. (Cl. Plt.—11)

This invention is of a new and distinct variety of hybrid rose plant developed by me in the course of extensive breeding efforts carried on since 1955 in nursery grounds at Livermore, California, with the object of producing a rose plant which would combine the vigor and habit of Queen Elizabeth (Plant Pat. 1,259) with the bud form and flower size of Yellow Perfection (Plant Pat. 1,083) in a multicolor rose with a yellow color base. Another object was to produce such a rose that would express the very strong and unusual fragrance of Yellow Perfection.

My new variety of rose plant originated as a seedling resulting from a cross of Queen Elizabeth, as the seed parent, with Yellow Perfection as the pollen parent and this particular plant was observed to have flowers that were larger than those of either Queen Elizabeth or Yellow Perfection, differing strikingly in having many more petals and a shape that was imbricate to irregularly imbricate instead of tending to be cup shaped, as are the flowers of Queen Elizabeth. In color, the flowers were found to be very distinct from either parent with a coloration pattern generally intermediate between that of Peace (Plant Pat. 591) and Angel Wings (Plant Pat. 1,865) and differing from both in that the flowers darkened with age to take on a distinctive intensification of the carmine pigmentation, thus giving the two or three day old flower a beauty comparable to that of the opening stages wherein the long urn shaped buds, upon opening, displayed petals having a sulfur yellow color at the base which gradually transformed to a rose madder color at the petal margins so as to give the opening flower a beautiful and delicate multicolor effect.

These distinctive characteristics, together with other advantages hereinafter described, including the long urn-shaped form of the buds, which resemble the buds of the older varieties of Soeur Therese (not patented) and Eclipse (Plant Pat. 172) and are an improvement over the short ovoid bud of Queen Elizabeth, Yellow Perfection and Peace, led to the selection of this plant for propagation and trial and asexual propagation of this plant, by budding, through successive generations has demonstrated that the novel and distinctive characteristics of the new variety are consistent and firmly fixed.

Asexual propagation of this new variety was first carried on at Livermore, California, under my direction, and present propagation, by budding, is done at growing grounds in Shafter, California.

My new variety of rose plant is illustrated in the accompanying full color drawing which shows foliage as well as the form of the buds and the fully opened bloom; and the following is a detailed description of the new variety as grown at Livermore, California, with color designations according to the Horticultural Color Chart of the British Color Council, unless otherwise stated.

*The plant*

Origin: Seedling.

Parentage:

*Seed parent.*—"Queen Elizabeth" (P.P. 1,259).

*Pollen parent.*—"Yellow Perfection" (P.P. 1,083).

Classification:

*Botanic.*—Cross of grandiflora × hybrid tea.

*Commercial.*—Grandiflora.

Form: Bush, 5 to 6 feet tall.

Growth: Very vigorous, very erect, with compact habit similar to that of Queen Elizabeth.

Branching: New branches, which start out from the base at 45 to 80 degree angles, curve rapidly upwardly to provide the tall compact growth habit.

Strength: Very strong with heavy canes ⅜" to ½" in diameter.

Foliage:

*Quantity.*—Abundant. Plant is well clothed with many leaves.

*Size of leaf.*—Large, 4" to 8".

*Leaflets.*—Size: Large—1½" wide x 1½" to 2½" long. Number: 5 to 7. Ribs and veins: Prominent only on lower surface and bronze red in color. Petioles: Length 1" to 1½". Rachis: ¼" to ⅜" wide x ¾" to 1" long, stipules inclined forwardly at about 55 to 65 degree angle. Shape: Oval elongate; essentially singly serrate with teeth 1/16" long. Texture: Leathery and glossy. Color: Upper side—near spinach green (0960) but darker, and tinged with bronze-red pigment especially near margins; under side—near spinach green (0960/3), larger veins are bronze red. Plant has thorns, spines and prickles. Size of thorns: Large, about ½" to ⅝" long; curved, but only occasionally curved downward. Color of thorns: Medium brown.

*Bud*

Form: Long, pointed at first and becoming urn-shaped when it begins to open. Opens slowly to a well imbricated flower at ¼-open stage.

Size: Length 1½" to 2". Diameter 1" to 1½".

Color: When sepals first divide—sulfur yellow (1) at base to rose madder (23). When petals begin to unfurl—same color at base, inside surface of petals now appears tinged with camellia rose (622/2). The color transition from base to margin of the petal is a very gradual one, giving the opening flower a delicate multicolor effect.

Sepals: Hooded over bud. Clasping until petals show color, then begin to turn downward either with all at right angles to long axis of bud or with two sepals curled back parallel with the peduncle.

*Shape.*—Spear shaped—1¾" long x ⅜" wide at base, with 4 to 5 lance shaped appendages on each side. Basal appendages ⅛" to ¼" long.

*Color.*—Inside—near carnation green (00058). Outside—Scheele's green (860) with ⅛" to ¼" at base heavily tinged with bronze red pigment.

*Hypanthium.*—Funnel-shaped about ½" long x ¾" diameter at top. Medium green color—near Plate 20H6 of A. J. Maerz Dictionary of Color (1950). Appearing glabrous but having minute (1/32") greyish hairs. Does not split.

*Peduncle.*—Strong and erect. 2" to 3" long with many small (1/16") prickles. Color: Lettuce green (861/1–3) heavily tinged with bronze red pigment.

*Flower*

Blooming habit: Plant blooms profusely from early spring through late fall and is at its best during the fall season.

Size: Very large. Diameter 4½" to 5"; depth 2¼" to 2½".

Borne: Singly and in clusters of 2 to 5 blooms per cluster.

Shape: High center when first opened. Changing later to become irregularly imbricate with the center petals remaining folded along midrib and covering stamens and pistils.

Petalage: 40 to 65 petals of obovate form arranged with the outer petals regularly imbricate and the inner petals irregularly imbricate.

*Color.*—Outer petals—generally cream white with sulfur yellow (1/1) base and with margins tinged carmine (21/1). Inside petals—sulfur yellow (1/1) to Naples yellow (403/2). Reverse side—same except area of sulfur yellow at base is somewhat smaller. Also petal margins are not so heavily tinged with carmine.

*Petaloids.*—10 to 15 in number, ½" to ¾" x ⅞" to 1¼" in size. Flowers with only 40 petals usually have more and smaller petaloids. Color same as petals.

*Texture.*—Soft. Appearance—satiny.

*Discoloration.*—Darkens to carmine (21) coloration over most of the petal surface, freckled with darker red in ⅛" to ¼" circular areas.

*Peduncle.*—2" to 3" long. Sturdy and upright. Color—green tinged purple red on side exposed to sun.

*Stem.*—10" to 12" long.

Effect of weather: The flower opens best in hot weather with more regular imbrication and daintier coloration. Color is also affected by climatic conditions, the colors all being richer in a warm dry climate and lighter in a cool moist climate.

Fragrance: Only slight, reminiscent of Yellow Perfection.

Lasting quality: 4 to 5 days on plant; 3 to 4 days as a cut flower.

Persistance: Drops petals clean.

Disease resistance: Resistant to mildew, as observed in growing fields at Livermore and at Shafter, California.

*Genital organs*

Stamens: Anthers—55 to 60 irregularly arranged and of ⅛" to ¼" in length. Filaments—⅛" to ¼" long and of chrome yellow color.

Pollen: Golden yellow in color.

Pistils: 60 to 75 in number—¼" to ⅜" long.

Stigmas: Greenish yellow in color.

Ovaries: Many, small and infertile ovaries.

*Fruit*

The fruit fertile, round in shape, and of a deep yellow color at maturity.

My herein described new variety of rose plant resembles Peace (P.P. 591) in the general coloration of the flower and the seed parent, Queen Elizabeth, in habit. The new variety also somewhat resembles Angel Wings (P.P. 1,865) in coloration, but differs from both Angel Wings and Peace in that the color of the petals darkens as they age with the carmine pigmentation intensifying progressively to provide a continuously changing color effect.

This rose plant is similar to Queen Elizabeth in growth and flowering habit, as well as in quantity and continuity of flower production. The leaves are larger, more leathery, and somewhat glossy but not as much so as the leaves of Queen Elizabeth. Also they differ in form, the leaflets being more elongate, and they are much more heavily tinged with bronze red pigment. The thorns are very similar to those of Queen Elizabeth, but turn brown much earlier as the cane matures.

The new variety is a strong hardy plant growing rapidly to form a tall compact bush having an abundance of continuously blooming flowers which provide a kaleidoscopic effect in brilliant colors. This new variety grows well over a wide range of climatic conditions, although there is some variation of color intensity of the blooms, the deeper richer coloration occurring in the warm-dry Southern climates.

Having thus shown and described my new variety of rose plant, I claim:

A new and distinct variety of rose plant, substantially as herein shown and described, distinguished by its combination of the long urn-shaped bud which opens to a multicolor yellow, gold and carmine coloration in a large high centered imbricate flower with the tall compact habit of growth, plant vigor, and continuity of abundant blooms that is characteristic of Queen Elizabeth.

No references cited.

ABRAHAM G. STONE, *Primary Examiner.*

R. E. BAGWILL, *Assistant Examiner.*